US00PP11815P2

(12) United States Plant Patent
van Rijn

(10) Patent No.: US PP11,815 P2
(45) Date of Patent: Mar. 13, 2001

(54) ANTHURIUM PLANT NAMED 'MARS'

(75) Inventor: Leonardus van Rijn, Schipluiden (NL)

(73) Assignee: RijnPlant, Schipluiden (NL)

( * ) Notice: Subject to any disclaimer, the term of this patent is extended or adjusted under 35 U.S.C. 154(b) by 0 days.

(21) Appl. No.: 09/291,094

(22) Filed: Apr. 14, 1999

(51) Int. Cl.[7] ..... A01H 5/00

(52) U.S. Cl. ..... Plt./369

(58) Field of Search ..... Plt./369, 365

(56) References Cited

PUBLICATIONS

UPOV–RON GTIM Computer Database 1999/02, GTI Jouve Retrieval Software, citation for 'Mars', May 1998.*

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Anthurium plant named 'Mars', characterized by its upright plant habit; freely clumping growth habit; large, durable dark green leaves that are ovate in shape; large and numerous spathes that are positioned upright and beyond the foliage on strong and erect scapes; durable, glossy dark red spathes; year-round continuous flowering; good flowering under low light conditions; and good post-production longevity.

1 Drawing Sheet

BACKGROUND OF THE INVENTION

The present invention relates to a new and distinct cultivar of Anthurium plant, botanically known as *Anthurium andreanum*, and hereinafter referred to by the cultivar name 'Mars'.

The new Anthurium is a product of a planned breeding program conducted by the Inventor in Schipluiden, The Netherlands. The objective of the program is to create and develop new Anthurium cultivars that have a freely clumping growth habit, strong and vigorous plant growth, attractive spathe color, numerous inflorescences and leaves, and good post-production longevity.

The new Anthurium originated from a cross by the Inventor in January, 1995 of the Inventor's proprietary *Anthurium andreanum* selection code No. 93-27 as the female, or seed, parent with the Inventor's proprietary *Anthurium andreanum* selection code No. 00-25 as the male, or pollen, parent. The cultivar 'Mars' was discovered and selected by the Inventor as a plant within the progeny of the stated cross in a controlled environment in Schipluiden, The Netherlands in February, 1998.

Asexual propagation of the new cultivar by tissue culture in a laboratory in Belgium has shown that the unique features of this new Anthurium plant are stable and reproduced true to type in successive generations of asexual propagation.

BRIEF SUMMARY OF THE INVENTION

The new Anthurium has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar 'Mars'. These characteristics in combination distinguish 'Mars' as a new and distinct cultivar:

1. Upright plant habit.
2. Freely clumping growth habit.
3. Large, durable dark green leaves that are ovate in shape.
4. Large and numerous spathes that are positioned upright and beyond the foliage on strong and strong and erect scapes.
5. Durable, glossy dark red spathes.
6. Year-round continuous flowering.
7. Good flowering under low light conditions.
8. Good post-production longevity.

The new Anthurium can be compared to the female parent, the Inventor's proprietary selection code No. 93-27. In side-by-side comparisons conducted by the Inventor in Schipluiden, The Netherlands, plants of the new Anthurium differ from plants of selection code No. 93-27 in the following characteristics:

1. Plants of the new Anthurium are more compact than plants of the selection code No. 93-27.

2. Plants of the new Anthurium have more durable leaves than plants of the selection code No. 93-27.

3. Plants of the new Anthurium have larger spathes than plants of the selection code No. 93-27.

4. Plants of the new Anthurium have dark red-colored spathes whereas plants of the selection code No. 93-27 have pink-colored spathes.

The new Anthurium can be compared to the male parent, the Inventor's proprietary selection code No. 00-25. In side-by-side comparisons conducted by the Inventor in Schipluiden, The Netherlands, plants of the new Anthurium differ from plants of selection code No. 00-25 in the following characteristics:

1. Plants of the new Anthurium are more compact than plants of the selection code No. 00-25.

2. Plants of the new Anthurium have smaller and more durable leaves than plants of the selection code No. 00-25.

3. Plants of the new Anthurium have dark red-colored spathes whereas plants of the selection code No. 00-25 have dark pink-colored spathes.

The new Anthurium can be compared to the Anthurium cultivar 'Elisabeth', disclosed in U.S. Plant Pat. No. 9,704. In side-by-side comparisons conducted by the Inventor in Schipluiden, The Netherlands, plants of the new Anthurium differ from plants of the cultivar 'Elisabeth' in the following characteristics:

1. Plants of the new Anthurium are more compact than plants of the cultivar 'Elisabeth'.

2. Plants of the new Anthurium have more durable leaves than plants of the cultivar 'Elisabeth'.

3. Plants of the new Anthurium and the cultivar 'Elisabeth' differ in spathe lobe coloration.

BRIEF DESCRIPTION OF THE PHOTOGRAPH

The accompanying colored photograph illustrates the overall appearance of the new Anthurium, showing the colors as true as it is reasonably possible to obtain in colored reproductions of this type. The photograph comprises a top perspective view of a typical potted plant of the cultivar 'Mars'. Leaf, spathe and spadix colors in the photograph may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe 2.5-year old plants grown in 30-cm containers in Schipluiden, The Netherlands, in a glass greenhouse with an average day temperature of 25° C. and an average night temperature of 19° C.

Botanical classification: *Anthurium andreanum* cultivar 'Mars'.

Parentage:

*Female parent*.—Inventor's proprietary *Anthurium andreanum* selection code No. 93-27.

*Male parent*.—Inventor's proprietary *Anthurium andreanum* selection code No. 00-25.

Propagation:

*Method*.—By tissue culture.

*Time to develop roots*.—About 70 or 84 days at 24° C. or 21° C., respectively are required to root a tissue-cultured plantlet.

*Rooting habit*.—Numerous and very strong fleshy roots.

Plant description:

*Plant shape*.—Upright, inverted triangle, symmetrical.

*Growth habit*.—Freely clumping, bushy and dense. Appropriate for 17 to 40-cm containers.

*Plant height*.—About 60 cm from soil level to leaf plane and about 60 to 85 cm from soil level to apex of spathes.

*Plant width*.—About 100 to 120 cm.

*Plant vigor*.—High.

*Growth rate*.—Rapid.

*Crop time*.—About 8 and 16 months are usually required from planting of young plants to finished plants in 17 and 40-cm containers, respectively.

*Foliage description*.—Quantity: Usually about two to four per shoot. Length: About 30 to 42 cm. Width: About 17 to 23 cm. Shape: Ovate. Apex: Apiculate. Base: Strongly auriculate; lobes not overlapping. Margin: Entire. Surface: Slightly undulating. Texture: Smooth, glabrous, leathery. Color: Young leaves, upper surface: Darker than 137A; glossy. Young leaves, lower surface: Darker than 137A; somewhat glossy. Mature leaves, upper surface: Darker than 137A. Mature leaves, lower surface: Darker than 147B to 147C with gray and reddish flush. Petiole: Length: About 35 to 55 cm. Color: Close to 146B; slight anthocyanin. Geniculum length: About 2.5 to 4.5 cm. Geniculum diameter: About 5 to 7 mm. Geniculum color: 146A to 144A; older leaves, dark purple anthocyanin.

Inflorescence description:

*Inflorescence arrangement*.—Spathes with spadices held beyond the foliage. Flowering structures arise from leaf axils. Freely flowering; continuous flowering year-round; numerous spathes/spadices per plant.

*Inflorescence longevity*.—Spathes/spadices last about six weeks under winter conditions and about three months under summer conditions; persistent.

*Flowers*.—Quantity per spadix: Numerous, about 200. Shape: Rounded. Diameter: About 1 mm, maximum.

*Spathe*.—Length: About 18 to 24 cm. Width: About 16 to 20 cm. Shape: Cordate to ovate. Apex: Apiculate. Base: Very strongly auriculate; lobes not overlapping. Margin: Entire. Texture: Leathery, glabrous, slight blistering, glossy. Color: When opening: 45A. Front surface: 45A; lobes becoming green, close to 144A, and darker green with development. Back surface: 47A to 45B. After senescence: 46B; lobes, dark brown greenish red, R.H.S. Colour Chart value not available.

*Spadix*.—Length: About 6 to 8 cm. Diameter: Midsection, about 10 to 11 mm; apex, about 8 mm. Shape: Columnar. Cross section: Rounded. Longitudinal axis: Very weakly recurved. Color: Immature: 159B. Base and mid-section: 47D. Apex: 33A. After senescence: 146C to 151C.

*Scape*.—Length: About 45 to 55 cm. Aspect: Strong and erect. Color: 144A; slight anthocyanin at apex, purplish.

*Reproductive organs*.—Androecium: Pollen color: Creamy white, 158D. Gynoecium: Stigma shape: Ovoid. Ovary: Protogyneous.

Disease resistance: Plants of the new Anthurium have exhibited good resistance to root diseases common to Anthurium.

Seed development: Seed development on plants of the new Anthurium has not been observed.

It is claimed:

1. A new and distinct cultivar of Anthurium plant named 'Mars', as illustrated and described.

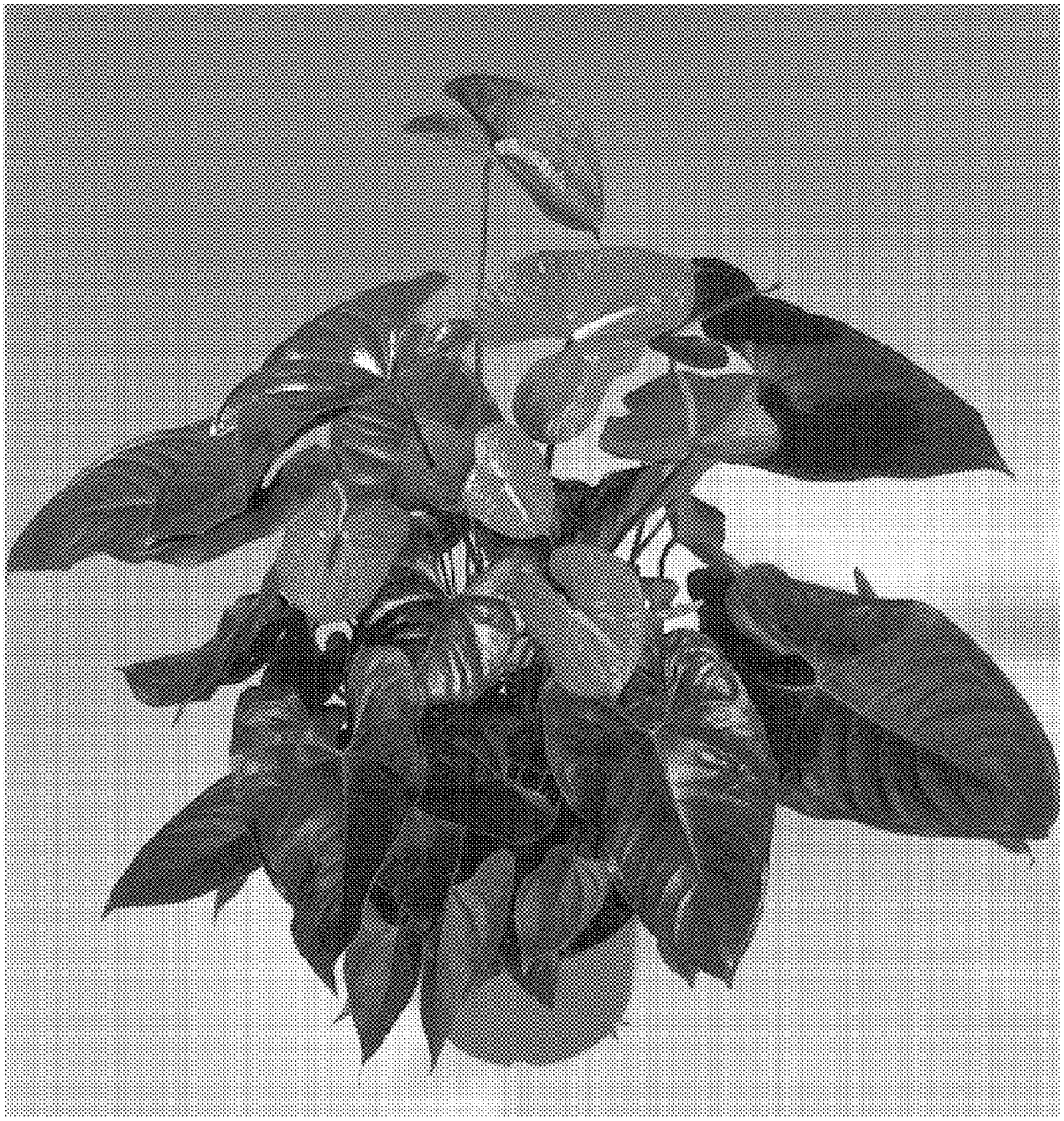

* * * * *